United States Patent

Dittrich et al.

[11] Patent Number: 6,126,359
[45] Date of Patent: Oct. 3, 2000

[54] BAYONET COUPLING FOR DETACHABLE JOINING OF TWO TUBULAR SHAFT INSTRUMENTS OR INSTRUMENT PARTS

[75] Inventors: Horst Dittrich, Immendingen; Frank Doll, Dürbheim, both of Germany

[73] Assignee: Karl Storz GmbH & Co. KG, Germany

[21] Appl. No.: 09/028,978

[22] Filed: Feb. 25, 1998

[30] Foreign Application Priority Data

Feb. 25, 1997 [DE] Germany .......................... 197 07 373

[51] Int. Cl.⁷ ............................................... B25G 3/16
[52] U.S. Cl. ........................... 403/349; 403/325; 403/353
[58] Field of Search .................................. 403/349, 348, 403/325, 321, 353, DIG. 4; 604/22, 167, 180

[56] References Cited

U.S. PATENT DOCUMENTS

| | | | |
|---|---|---|---|
| 2,901,258 | 8/1959 | Brandafi | 403/349 X |
| 4,943,182 | 7/1990 | Hoblingre | 403/349 |
| 4,986,690 | 1/1991 | Cooksey | 403/325 X |
| 5,407,293 | 4/1995 | Crainich | 403/325 X |

FOREIGN PATENT DOCUMENTS

| | | |
|---|---|---|
| 0 705 571 A1 | 3/1995 | European Pat. Off. . |
| 43 07 539 A1 | 9/1994 | Germany . |
| 43 23 093 A1 | 1/1995 | Germany . |

*Primary Examiner*—Lynne H. Browne
*Assistant Examiner*—David E. Bochna
*Attorney, Agent, or Firm*—St. Onge Steward Johnston & Reens LLC

[57] ABSTRACT

A bayonet coupling (10) is used for detachable joining of two tubular-shaft instruments or instrument parts. A bayonet sleeve (12) (female part), having a bayonet guide (14), is provided on the one instrument or instrument part, and a bayonet insert (52) (male part) is provided on the other instrument or instrument part. An interlock system serves to lock the bayonet coupling (10) in the closed state. It is proposed that the interlock system have an interlock piece (28), displaceable along the bayonet sleeve (12), which comes directly into inhibiting engagement with the bayonet insert (52) inserted into the bayonet sleeve (12), in the insert's terminal position, and inhibits the bayonet insert (52) from rotating; and which can be moved away from the bayonet insert (52) in order to release the interlock system (FIG. 1).

6 Claims, 2 Drawing Sheets

BAYONET COUPLING FOR DETACHABLE JOINING OF TWO TUBULAR SHAFT INSTRUMENTS OR INSTRUMENT PARTS

FIELD OF THE INVENTION

The invention concerns a bayonet coupling for detachable joining of two tubular-shaft instruments or instrument parts, with a bayonet sleeve (female part), having a bayonet guide, on the one instrument or instrument part, and a bayonet insert (male part) on the other instrument or instrument part; and with an interlock system to lock the bayonet coupling when closed.

BACKGROUND OF THE INVENTION

A bayonet coupling of this kind is known from DE 43 07 539 A1.

In medical technology, there is an increasing demand for instruments, and in particular for tubular-shaft instruments, which can be disassembled with a few actions in order to clean and sterilize the instruments after an operation. In addition, modular designs have gained a foothold in medical technology; for example, a variety of instrument parts such as blades, gripping forceps, or the like can be mounted on at the distal end on tubular-shaft instruments having scissor-like handles.

In minimally invasive surgery, it is often necessary to insert an endoscope, a trocar, a forceps, a scissors, or another instrument into a shaft which can, for example, be a universal shaft, a trocar sleeve, or the like. It is necessary in this context that the instrument joined to the shaft be immovably joined to the shaft during use, and that it be easily capable of being detached again when necessary.

A coupling is provided in order to create this immovable join. These couplings are generally configured as bayonet couplings, i.e. a bayonet sleeve (female part) having a bayonet guide is provided on one of the tubular-shaft instruments or instrument parts, and a bayonet insert (male part) is inserted or twisted into this.

Interlock systems are provided so that the bayonet coupling is not disconnected during handling by rotation of the coupled parts relative to one another.

In the case of DE 43 07 539 A1 cited initially, the bayonet sleeve is provided at the distal end of a tubular shaft of a forceps. The bayonet insert is provided at the distal end region of a rod-shaped actuation element that carries the forceps jaw parts at the distal end. The proximal end of the rod-shaped actuation element is used for joining to a movable grip element of the handle, which is scissor-like or configured otherwise. When these two parts are coupled, the proximal end of the rod-shaped actuation element is pushed distally into the shaft and through it until the bayonet insert comes into engagement with the bayonet sleeve. Once the bayonet insert has been slid into the bayonet guide of the bayonet sleeve and rotated, the two components are interlocked in this position. For this, there are provided at the proximal end of the rod-shaped actuation element two axially extending flattened areas, into which are recessed radial clamping elements which are held in the clamping position by means of a spring washer. The clamping elements prevent any relative rotation between shaft and rod-shaped actuation element.

This interlock system is cumbersome to handle, and requires dimensionally accurate machining of the draw-in bar and the sleeve at the proximal end.

Because the actual bayonet coupling is arranged at the distal end, but the interlock system is at the proximal end of the tubular-shaft instrument, torques acting on the tubular-shaft instrument can nevertheless cause loosening of the coupling. The rod-shaped actuation element has, with ordinary forceps, diameters in the range of a few millimeters, but lengths in the range of 20 cm and more. In other words, the coupling is located at an axial distance of approximately 20 cm from the interlock system. Torques can now cause torsion of the long, thin rod-shaped actuation element such that the distal end of the rod is rotated sufficiently, relative to the locked proximal end, for the coupling to release.

Torques of this kind act on instruments when a piece of tissue, for example cartilage, is grasped with, for example, the instrument part operating at the distal end, and the intention is to detach the piece of tissue being grasped by closing and rotating the instrument.

DE 43 23 093 A1 discloses a similar surgical forceps in which the bayonet coupling is also provided at the distal end, and the interlock system at the proximal end. The interlock system is carried out in such a way that at the proximal end of the rod-shaped actuation element, an axially extending spring element is provided, which snaps into a longitudinal slot at the proximal end of the shaft. Here again, torsion of the rod-shaped actuation element can cause the coupling to release.

Such release can have fatal consequences for the patient, since the instrument can then no longer be actuated, and comes apart into two pieces inside the patient's body.

OBJECTS OF THE INVENTION

It is therefore the object of the present invention to develop a bayonet coupling of the kind cited initially in such a way that the interlock system is secure, and in particular can absorb high torques which act on the bayonet joint.

SUMMARY OF THE INVENTION

According to the invention, the object is achieved by the fact that the interlock system has an interlock piece, displaceable along the bayonet sleeve, which comes directly into inhibiting engagement with the bayonet insert pushed into the bayonet sleeve, in the insert's terminal position, and inhibits the bayonet insert from rotating; and which can be moved away from the bayonet insert in order to release the interlock system.

The interlock system is now no longer located away from the actual bayonet coupling, but rather takes place directly at the coupling. Decouplings due to torsional movements of components between the bayonet coupling and interlock system are thus fundamentally ruled out. Because the interlock system comes into inhibiting engagement directly with the bayonet insert, very high torques can be absorbed. Because the interlock piece is displaceable only axially, i.e. along the bayonet sleeve, and comes into inhibiting engagement with the bayonet insert in the latter's terminal rotational position, there is no possibility for the bayonet insert to rotate out of its terminal rotational position. This would be a requirement, however, for the bayonet joint to release, i.e. the bayonet insert must first be rotated a certain amount, but this is now effectively inhibited.

In addition, closing and release of the coupling can easily be carried out by displacing the interlock piece axially along the bayonet sleeve, either in the direction of the inhibiting position in order to lock, or in the opposite direction to release the interlock system. The bayonet coupling with the interlock system is a compact component, i.e. all components are confined to the region of the bayonet coupling.

This also allows for a very flexible arrangement of the bayonet coupling, be it at the distal or at the proximal end of a tubular-shaft instrument or even between them, as desired.

The coupling is now also independent of whether or not a rod-shaped actuation element, as described initially, is present. The coupling now being proposed operates independently of components having other functions, and is thus substantially more universal and more reliably usable.

The object is thus completely achieved.

In a further embodiment of the invention, the interlock piece is acted upon by the force of a spring which pushes the interlock piece into inhibiting engagement with the bayonet insert.

The advantage of this feature is that the interlock piece is continuously pushed into the inhibiting position, so that a closed coupling is locked in securely inhibiting fashion. To release the coupling, the interlock piece must first be pulled, against the force of the spring, away from the bayonet insert, and only then can the latter be rotated. This is possible by means of an easily managed displacement movement along the tubular-shaft instrument, with no need for other manipulations such as, for example, disassembly of the shaft or disassembly of grip elements.

In a further embodiment of the invention, the interlock piece is joined to an outer sliding sleeve which can be grasped and displaced manually.

This feature guarantees, in a particularly physically simple manner, the aforementioned advantages of simple handling to release the coupling.

In a further embodiment of the invention, the interlock piece has, on the side facing the bayonet insert, a recess which, in the terminal position of the bayonet insert, can be slid onto an end section of the bayonet insert; and once slid on, the interlock piece inhibits rotation of the bayonet insert.

The advantage of this feature is that an interlock system of compact structure is possible, which offers sufficient rotation prevention even for thin tubular-shaft instruments, i.e. can absorb high torques.

In a further embodiment of the invention, the interlock piece has an end face, facing the bayonet insert, such that the bayonet insert inserted into the bayonet sleeve first pushes the interlock piece back and can be rotated relative to the interlock piece into the terminal position.

The advantage of this feature is that control and displacement of the interlock piece are accomplished by the bayonet insert itself, with no need, for the purpose, for further physical components. The bayonet insert pushes the interlock piece back after it has met its end face, and can be rotated relative to the interlock piece until the interlock piece can be slid axially onto the bayonet insert, which then occurs automatically in the case of the embodiment having the spring-loaded interlock piece. This means that for interlocking, the operator needs to perform no movements other than those to carry out the bayonet coupling, i.e. insertion and rotation; interlocking then takes place automatically at the end of the rotational movement of the bayonet insert. For release, correspondingly, all that is necessary is to displace the interlock piece, in the embodiment with the outer sliding sleeve, by hand in order to release the coupling.

In a further embodiment of the invention, the interlock piece has a centered continuous bore.

The advantage of this feature is that components, for example a rod-shaped actuation element, can pass through the interlock piece, so that the bayonet coupling can then be arranged at any specific axial point on a tubular-shaft instrument having an actuation element of this kind.

For this purpose, all components are then equipped with a continuous bore or opening.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

The invention will be described and explained in more detail below with reference to a selected exemplifying embodiment. In the drawings.

DETAILED DESCRIPTION OF THE INVENTION

Figure 1:
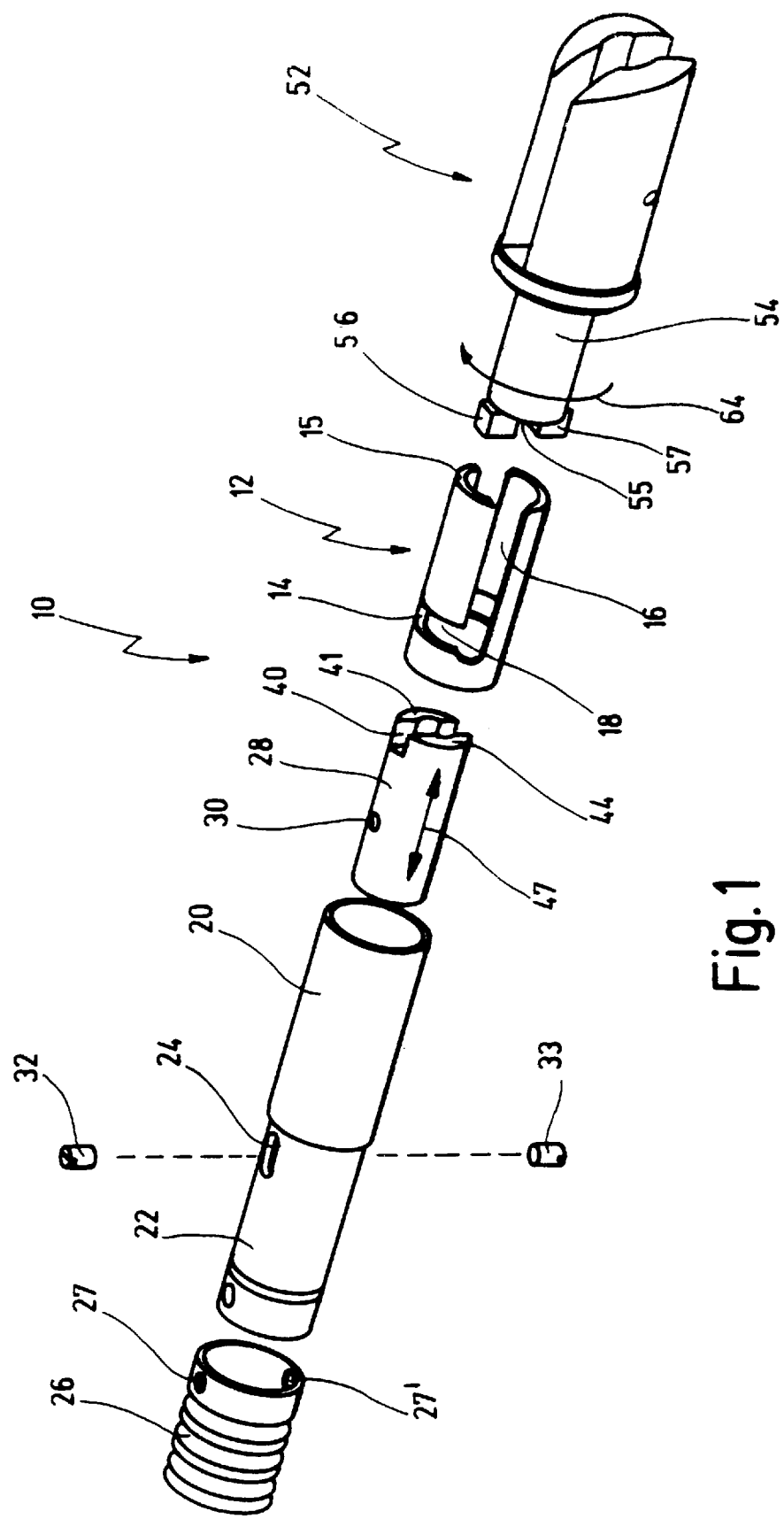
FIG. 1 shows, in an exploded view, the essential components of a bayonet coupling according to the invention.

A bayonet coupling, assigned the reference number 10 in the Figs., has a bayonet sleeve 12, which constitutes a female part of the coupling 10.

Provided in bayonet sleeve 12 is a bayonet guide 14 which has in each case, located diametrically opposite, a longitudinal slot 16, proceeding from an insertion end 15, which continues at its closed rear end into a transverse slot 18, as is common in bayonet guides.

Figure 2:
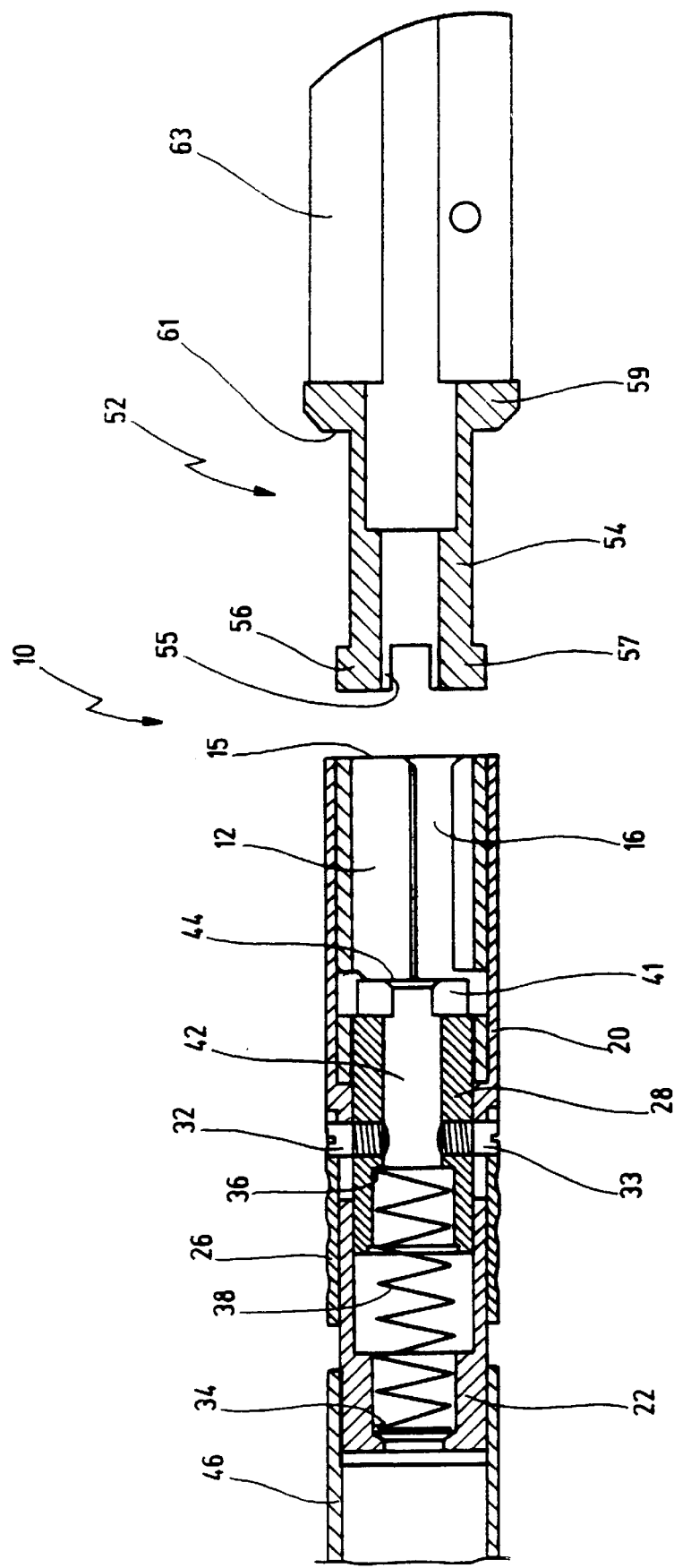
FIG. 2 shows a longitudinal section through the two components, as installed but not yet coupled together.

Bayonet sleeve 12 is received in a sleeve 20 and joined non-rotatably thereto (see sectioned view in FIG. 2).

Sleeve 20 continues into a slightly smaller-diameter tubular piece 22, on whose exterior two longitudinal slots 24 are provided diametrically opposite one another.

A sliding sleeve 26, whose open inside diameter corresponds approximately to the outside diameter of tubular piece 22, can be slid onto smaller-diameter tubular piece 22. Diametrically opposite holes 27 and 27', which line up with longitudinal slots 24, are provided in sliding sleeve 26. Also received in the interior of sleeve 20 is a hollow cylindrical interlock piece 28 which also has diametrically opposite threaded bores 30 which line up with longitudinal slots 24 of tubular piece 22 and with holes 27, 27' of sliding sleeve 26.

In the assembled state (see FIG. 2), interlock piece 28 is slid into tubular piece 22, and sliding sleeve 26 is slid onto its exterior; this takes place in such a way that bores 30 in the interlock piece line up with longitudinal slots 24 and with holes 27, 27' in sliding sleeve 26. Sliding sleeve 26 is joined immovably to interlock piece 28 by threading in screws 32 and 33.

The assembly made up of sliding sleeve 26 and interlock piece 28 is, however, displaceably axially back and forth, corresponding to the length of longitudinal slots 24, as indicated by double arrow 47.

As is evident from the sectioned view in FIG. 2, a buttress 34 in the form of a blind hole is provided in the interior of tubular piece 22, opposite which is a corresponding buttress 36 in interlock piece 28.

These buttresses 34 and 36 serve as bracing points for a helical spring 38 which is preloaded in compression when assembled (FIG. 2).

As a result of the compressive force of spring 38, the assembly made up of sliding sleeve 26 and interlock piece 28 is thus pushed in the direction of the insertion end of bayonet sleeve 12.

At the end facing the insertion end of bayonet sleeve 12, interlock piece 28 has a recess 40. Recess 40 corresponds to a radial centered indentation, so that axially extending projections 41 are present on either side of recess 40.

The region of recess 40, and projections 41 flanking it, lie in the region of transverse slot 18 of bayonet guide 14, as is apparent in particular from the sectioned view of FIG. 2.

Interlock piece 28 has, on this end facing the insertion end of bayonet sleeve 12, a smooth, flat end face 44.

The aforementioned assembly is provided at the distal end of a shaft 46 of a tubular-shaft instrument, for example a medical forceps.

Bayonet coupling 10 moreover has a bayonet insert 52, which constitutes a male part of the coupling.

Bayonet insert 52 has a hollow cylindrical section 54 in whose end section 55 are provided lugs 56 and 57, protruding radially beyond the hollow cylindrical section.

The contour of lugs 56 and 57 is selected so that they can be introduced to fit into the bayonet guide. At the end opposite lugs 56 and 57, hollow cylindrical section 54 is equipped with a shoulder 59 which constitutes a stop 61.

Hollow cylindrical section 54 continues to extend into a mounting extension 63. Mounted on the mounting extension is a distal working element; in the aforementioned example of a medical forceps, this consists of appropriate forceps jaw elements.

It is evident from the sectioned view in FIG. 2 that both components of bayonet coupling 10 have a central continuous opening through which, for example, a rod-shaped actuation element can be slid in order to actuate the forceps jaw elements mounted on mounting extension 63.

To close bayonet coupling 10, bayonet insert 52 is rotated 90 degrees from the position shown in FIGS. 1 and 2, and placed on bayonet sleeve 12 in such a way that lugs 56 and 57 can engage into the diametrically opposite longitudinal slots 16 of bayonet guide 14. Bayonet insert 52 is slid forward until its end face meets end face 44 of interlock piece 28. Further insertion displaces interlock piece 28 against the force of spring 38 until lugs 56 and 57 are in front of transverse slot 18. The inserted bayonet insert 52 can now be rotated (see arrow 64), causing lugs 56 and 57 to enter transverse slots 18. When bayonet insert 52 has reached its terminal rotational position, i.e. the rotational position shown in FIGS. 1 and 2, its lugs 56 and 57 come to rest directly in front of recess 40 in end face 44 of interlock piece 28.

Spring 38 now pushes interlock piece 28 over lugs 56 and 57, so that the latter can then enter recess 40, which is then shaped accordingly, i.e. so that lugs 56 and 57 can fit into it.

In this inhibiting engagement between interlock piece 28 and bayonet insert 52, any rotation of bayonet insert 52 in bayonet sleeve 12 is inhibited. The force of compression spring 38 is set so that under ordinary handling, axial forces acting on sliding sleeve 26 are not sufficient to displace sliding sleeve 26 axially.

To release bayonet coupling 10, sliding sleeve 26 must simply be displaced against the force of spring 38, thus pulling interlock piece 28 away from lugs 56 and 57 of bayonet insert 52 so that the latter can then be rotated.

Sliding sleeve 26 can be released again after even a slight rotation of bayonet insert 52. Once lugs 57 and 57 have been rotated to the level of longitudinal slots 16, spring 38 assists in pushing bayonet insert 52 out of bayonet sleeve 12.

What is claimed is:

1. A bayonet coupling for detachable joining of two tubular-shaft instruments or two instrument parts, comprising a bayonet sleeve extending along a longitudinal axis and having a bayonet guide which is provided on a first instrument part, said bayonet guide having a distal end formed with an axially extending slot which continues in a transverse slot spaced from a proximal end of the bayonet guide, a bayonet insert provided on a second instrument part to be coupled with said first instrument part, the bayonet insert having a stud end provided with spaced apart lugs which extend axially from and radially outwardly from the stud to engage the longitudinal slot upon axial displacement of the instrument parts relative each other, the lugs having end walls, and an interlock piece having a distal end and being resiliently biased toward the second instrument part upon its insertion in said bayonet guide of said bayonet sleeve for locking engagement with said stud end of said bayonet insert to prevent said bayonet insert from rotating, said distal end of the interlock piece having an axial recess defining a floor and two axially extending and radially spaced apart lugs which extend along the longitudinal axis and abut said lugs of the bayonet insert upon axial displacement of the instrument parts so as the interlock piece and the bayonet insert are displaced axially in a terminal end position, wherein the lugs of the bayonet insert are aligned with the transverse slot of said bayonet guide upon angularly displacing of the first and second instrument parts relative to one another to an inhibiting position, wherein said interlock piece is forced toward said bayonet sleeve until the end walls of the lugs of the bayonet insert contact the floor of the axial recess of the interlock piece, wherein the axial lugs of the bayonet insert and the interlock piece are axially engaged and come into inhibiting engagement to arrest relative angular displacement of the instrument parts, said interlock piece being moveable away from said bayonet sleeve to release said bayonet insert.

2. The bayonet coupling of claim 1, wherein said interlock piece is acted upon by the force of a spring which pushes said interlock piece into inhibiting engagement with said bayonet insert.

3. The bayonet coupling of claim 1, wherein said interlock piece is joined to an outer sliding sleeve which can be grasped and displaced manually.

4. The bayonet coupling of claim 1, wherein said interlock piece has a centered continuous bore.

5. The bayonet coupling of claim 4, wherein said first and second instrument parts have a continuous central axial bore upon engagement of said instrument parts.

6. A coupling for detachably joining of two tubular-shaft parts, comprising:

an outer sleeve extending along an axis and having opposite ends, an interlock piece mounted rotationally fixed with and coaxial with the outer sleeve and having a distal end, the outer sleeve and the interlock piece being axially displaceable relative one another between inner and outer positions, the interlock piece being resiliently biased toward the outer position, the distal end of the interlock piece having two radially spaced apart arms defining an axial recess therebetween, the axial recess having a floor;

a guide sleeve mounted on the distal end of the interlock piece between the outer sleeve and the piece and rotationally fixed with the outer sleeve, the guide sleeve having a proximal end and a distal end provided with an axial slot which terminates in a transverse groove spaced from the proximal end; and an insert having a proximal end and two radially spaced lugs extending radially outwardly from the proximal end and axially therefrom to be guided in the axial slot until the lugs abut the arms of the interlock piece in the outer position, said lugs having end walls, and said lugs being aligned with the transverse groove upon further displacement of the insert and the interlock piece in the inner position thereof to enable their relative angular displacement relative to one another to an engaging position, wherein the arms are aligned with the recess allowing axial displacement of the interlock piece toward the outer position until the end walls of the lugs contact the floor of the axial recess to have the lugs and the arms come into inhibiting engagement, thus arresting the relative angular displacement.

* * * * *